(12) United States Patent
Effenberger et al.

(10) Patent No.: US 12,709,491 B2
(45) Date of Patent: Aug. 18, 2026

(54) APPARATUS AND METHOD FOR TREATING AND IN PARTICULAR STERILIZING CONTAINERS

(71) Applicant: KRONES AG, Neutraubling (DE)

(72) Inventors: Harald Effenberger, Schierling (DE); Alexander Feigl, Mintraching (DE); Florian Fuchs, Mehring (DE); Florian Hoffmann, Burglengenfeld (DE); Andreas Eichenseher, Deuerling (DE); Stefan Kornprobst, Dietfurt a.d. Altmühl (DE); Viktor Gette, Wörth an der Donau (DE); Wolfgang Schoenberger, Brennberg (DE); Andreas Vornehm, Offenberg (DE); Konrad Senn, Alteglofsheim (DE); Martin Kammerl, Hemau (DE); Michael Neubauer, Grassau (DE); Andreas Pense, Obertraubling (DE); Josef Knott, Schierling (DE); Thomas Kiendl, Maxhütte-Haidhof (DE)

(73) Assignee: KRONES AG, Neutraubling (DE)

( * ) Notice: Subject to any disclaimer, the term of this patent is extended or adjusted under 35 U.S.C. 154(b) by 28 days.

(21) Appl. No.: 18/757,126

(22) Filed: Jun. 27, 2024

(65) Prior Publication Data

US 2025/0002266 A1 Jan. 2, 2025

(30) Foreign Application Priority Data

Jun. 27, 2023 (DE) ..................... 10 2023 116 964.5

(51) Int. Cl.
*B65G 47/84* (2006.01)
*A61L 2/08* (2006.01)
(Continued)

(52) U.S. Cl.
CPC .............. *B65G 47/846* (2013.01); *A61L 2/08* (2013.01); *A61L 2103/23* (2026.01); *A61L 2202/122* (2013.01); *B65G 2201/0235* (2013.01)

(58) Field of Classification Search
None
See application file for complete search history.

(56) References Cited

U.S. PATENT DOCUMENTS 5,411,588 A * 5/1995 Diepens ................. G11B 23/00 118/712
7,712,601 B2 * 5/2010 Shimomura .......... B67C 7/0013 198/478.1

(Continued)

FOREIGN PATENT DOCUMENTS

DE 7523323 U 11/1975
DE 202013104114 U1 11/2013

(Continued)

OTHER PUBLICATIONS

Search Report issued German Patent Appln. Serial No. 10 2023 116 964.5, dated Jun. 7, 2024, with machine English translation, 8 pages.

(Continued)

*Primary Examiner* — Gene O Crawford
*Assistant Examiner* — Muhammad Awais
(74) *Attorney, Agent, or Firm* — HAYES SOLOWAY P.C.

(57) ABSTRACT

A container treatment apparatus for transporting plastic preforms along a predetermined transport path includes several transport devices, each of which has at least one holding element for holding a plastic container and guiding the plastic container along a portion of the transport path, wherein a second transport device immediately follows a first transport device along the transport path, and containers are transferred from a holding device of the first transport (Continued)

device to a holding device of the second transport device. The transport path along which the containers can be guided by the first transport device is arranged at least in portions outside a clean room, and the transport path along which the containers can be guided by the first transport device is surrounded at least in part by a radiation shielding device.

20 Claims, 6 Drawing Sheets

(51) Int. Cl.
*A61L 103/00* (2026.01)
*B65B 55/04* (2006.01)

(56) References Cited

U.S. PATENT DOCUMENTS

| | | | | |
|---|---|---|---|---|
| 8,336,703 | B2 * | 12/2012 | Pedrazzi | B65B 7/2814 198/470.1 |
| 8,418,836 | B2 * | 4/2013 | Papsdorf | B65G 47/846 198/479.1 |
| 8,931,621 | B2 * | 1/2015 | Krulitsch | B67C 3/242 198/478.1 |
| 2011/0278134 | A1 * | 11/2011 | Voth | B65G 47/847 198/478.1 |
| 2012/0070522 | A1 * | 3/2012 | Voth | B29C 49/46 425/88 |
| 2012/0168642 | A1 * | 7/2012 | Neuschwander | G21K 5/10 250/455.11 |
| 2014/0112826 | A1 * | 4/2014 | Knott | A61L 2/087 250/453.11 |
| 2015/0072041 | A1 * | 3/2015 | Scheuren | A61L 2/08 425/522 |

FOREIGN PATENT DOCUMENTS

| | | | | |
|---|---|---|---|---|
| DE | 102012110108 | A1 | 4/2014 | |
| DE | 202017105447 | U1 * | 12/2018 | B67C 3/22 |
| DE | 102021134541 | A1 * | 6/2023 | A61L 2/08 |
| EP | 2388129 | B1 | 5/2011 | |
| EP | 2845610 | A1 | 3/2015 | |
| JP | 2000214300 | A * | 8/2000 | |
| JP | 201610689 | A | 1/2016 | |
| JP | 7220152 | A | 2/2023 | |
| JP | 7220152 | B2 * | 2/2023 | A61L 2/087 |
| WO | 2008055375 | A1 | 5/2008 | |

OTHER PUBLICATIONS

Extended European Search Report issued in EP Patent Appln. Serial No. 24166940.7-1014, dated Sep. 27, 2024, with machine English translation, 11 pages.

* cited by examiner

APPARATUS AND METHOD FOR TREATING AND IN PARTICULAR STERILIZING CONTAINERS

BACKGROUND OF THE INVENTION

The present invention relates to a container treatment apparatus for transporting plastic containers, and in particular plastic preforms, along a predetermined transport path, wherein the container treatment apparatus has several transport devices, each of which has at least one holding element for holding a plastic container and guiding the plastic container on a portion of the transport path, wherein a second transport device (100) immediately follows a first transport device (4) along the transport path (T), and containers are transferable from a holding device of the first transport device (4) to a holding device of the second transport device (100). Furthermore, the invention relates to a method for treating containers, in particular for sterilizing containers.

Various container treatment apparatuses are known from the prior art. The treatment may, for example, include sterilization of the container surfaces. Often, preforms are treated in such a container treatment apparatus, which are then transformed into bottles or other containers in a subsequent step. This has the advantage that a comparatively small area needs to be treated. This is particularly advantageous in sterilization processes, as a smaller area needs to be sterilized, and sterilizing agents and/or energy can be saved upon.

The sterilization of containers usually takes place in a housing that is at least largely closed, in order to avoid contamination from outside. In this case, such a housing usually forms a so called clean room.

In some systems, at least one sterilization process involves an application with radiation. A radiation source provided for this purpose is also usually arranged at least in portions in a housing and emits the radiation into the interior of the housing, wherein the housing has shielding properties for this radiation. This allows people in the vicinity of such a sterilization device to be protected from scattered radiation. Typically, the housing having the shielding property for this radiation forms not only a boundary for the sterilizing radiation, but also the clean room boundary.

In particularly when sterilizing different regions of containers one after the other, the problem arises that all these devices should be arranged within the housing in order to avoid temporary contamination of the already sterilized surfaces. If several such sterilization devices are arranged within a common housing, they form a so called sterilization module. Due to the large number of sterilization devices and the transport devices for transferring individual containers from one sterilization device to the next, this is often very voluminous and requires a large amount of space.

From the applicant's internal prior art, it is known to sterilize plastic preforms on the outer and inner surfaces after heating them in an oven. By a particularly favorable arrangement of pitch varying starwheels, by which a distance between two containers directly following one another on the transport path can be set, and the guidance of the containers on different horizontal levels, the applicant has succeeded in providing a particularly compact sterilization module.

Furthermore, it is also known that the sterilization of a container to be filled is, in addition to the actual filling process, the central process step in an aseptic filling plant. In this case, ionizing radiation has proven to be particularly suitable for achieving the desired germ reduction. In most applications, this radiation consists of accelerated electrons that are generated in a corresponding facility and treat the containers to be sterilized, wherein systems used for sterilization usually consist of an electron generating apparatus and a beam finger for disinfecting the inner surfaces, as well as an electron generating apparatus and a surface emitter for disinfecting outer surfaces. In this case, the treatment devices for sterilizing the outer surfaces and the sterilization of the inner surfaces are each arranged on a carousel or transport starwheel.

In this case, the X-rays generated during sterilization—for example, by accelerated electrons—must be shielded from the environment by suitable shielding, so that the two treatment devices are embedded or housed in a radiation-shielding apparatus. Such a shielding device is described in more detail in EP 2 845 610 A1, for example. In the case of this shielding device, radiation shielding can also be ensured at the inlet and outlet of the sterilization module, since sufficient shielding surfaces are arranged between the radiation source and the inlet and outlet openings due to the inlet starwheel arranged upstream of the radiation treatment or the outlet starwheel arranged downstream of the radiation treatment.

Such an inlet starwheel or outlet starwheel is not provided for in the compact sterilization module known from the applicant's internal prior art. The sterilization of the containers takes place during transport of the containers by a transport starwheel, which is arranged directly at the inlet or outlet into or out of the housing. This allows the housing to be particularly compact, the transfer or transport route from the oven to the blow molding machine to be shortened, and thus the residence time of the containers in the treatment module to be reduced. However, the problem arises that (scattered) radiation can escape from the housing through the inlet and/or outlet opening.

There is therefore a need to provide a container treatment apparatus, in particular a container sterilization apparatus, which offers the advantages of the container treatment apparatus described above, which is compact and yet offers a high throughput of containers, but effectively reduces the emission of (X-ray) radiation. Such a container treatment apparatus should be as modular as possible and be compatible with other upstream or downstream container treatment apparatuses such as a blow molding device or a heating device. Furthermore, there is a need for a method for effective container handling on a short transport path.

SUMMARY OF THE INVENTION

A solution, according to the invention, to the underlying problem is thus provided by a container treatment apparatus for transporting plastic containers and in particular plastic preforms along a predetermined transport path. In this case, the container treatment apparatus has a plurality of transport devices, each of which has at least one holding element for holding a plastic container and guiding the plastic container on a portion of the transport path. In this case, a second transport device is arranged along the transport path directly following a first transport device, and containers can be transferred from a holding device of the first transport device to a holding device of the second transport device.

It is essential for a solution to the problem that the transport path along which the containers can be guided by the first transport device be arranged at least in portions outside a clean room, and the transport path along which the containers can be guided by the first transport device be surrounded at least in portions by a radiation shielding device.

This makes it possible for the environment in the region of the first transport device to be protected from radiation from the sterilization device without the entire first transport device having to be arranged in a clean room and/or a radiation-protective housing.

Preferably, the second transport device is part of a container surface sterilization device, in particular a container outer surface sterilization device. Preferably, a holding device of the second transport device can be brought at least temporarily into the region of an opening of a housing wall, in order to receive a container, to be brought into the space surrounded by the housing, from the first transport device. This makes it possible to transfer the container directly to a container surface sterilization device. This eliminates the need for an additional transport device which transfers the inserted container within the housing to the first container surface sterilization device following along the transport path.

In the following, a container surface sterilization device is also generally referred to as a container treatment device. All examples given for sterilization of a container surface should accordingly also be deemed to be disclosed for any other type of container treatment. In addition, all exemplary embodiments which are generally disclosed for a container treatment device are also to be considered as disclosed for the particularly preferred sterilization of a container surface, and thus a container surface sterilization device.

Preferably, a holding device of the second transport device is relatively movable with respect to a sterilization device—for example, a radiation source. Additionally or alternatively, in a particularly preferred embodiment, a position and/or orientation of a container in the region of the container outer surface treatment device can be changed with respect to a perpendicular projection of the transport path. This movement of containers relative to each other or with respect to the projection of the transport path enables, for example, a container to be rotated and/or tilted relative to a nozzle or radiation source in order to make previously shaded surface regions accessible to the container outer surface treatment device.

In a preferred embodiment, the first and/or the second transport device has a rotatable carrier. Such rotatable carriers are often used in particular in the field of bottle handling, and therefore this embodiment offers a particularly good possibility of integrating the container handling apparatus into existing systems or those to be newly equipped. Preferably, the axes of rotation of the first and/or the second transport device run substantially parallel—in particular preferably, exactly parallel. This design makes it possible to achieve particularly smooth running, relative to one another, of the carriers that follow one another directly along the transport path.

Preferably, the first and/or the second transport device has a plurality of holding elements. This makes it possible to transport and/or treat several containers during a recurring movement of the respective transport device, which increases the throughput.

In a preferred embodiment, the first and/or second transport device has a plurality of holding elements arranged on this carrier and which can be guided on a circular path and/or on an orbit at a variable distance from the center. In the following, the term "circular path" shall also be understood to mean an orbit around a center as mentioned above, in which slight deviations from the ideal circular orbit exist in one or more sectors. These can occur, for example, as described below, by individually changing the distance of individual holding elements from the center—for example, in order to flatten the circular path in certain regions or even to enable a largely linear guidance of holding elements and the containers arranged on them in a sector. Preferably, a holding element in a first sector of this circular path, in which a container is picked up, has a height, relative to a perpendicular projection of the transport path, which is different from that in a second sector in which a container is delivered. This makes it possible for a container to be picked up at a different height (with respect to the perpendicular projection of the transport path) than its delivery. This can be advantageous if the transport devices adjacent along the transport path are at different height levels.

In a preferred embodiment, a path on which a holding element of the first transport device can be guided changes its radius of curvature at least once, preferably several times. Such a change in the radius of curvature can include a change from a strong radius of curvature to a small radius of curvature (with the same sign and thus the same direction of curvature), and vice versa. In particular, however, it is preferred that the radius of curvature change its sign (i.e., the direction of curvature) at least once. By changing the radius of curvature, the radiation shielding device can be particularly effective in preventing incoming radiation from escaping into the environment. This can be achieved by ensuring that the radiation is reflected and/or absorbed particularly effectively in regions having a particularly strong radius of curvature. Preferably, the radiation shielding device forms a radiation trap by changing the radius of curvature and/or the direction of curvature (if necessary, several times). Preferably, the radiation is reflected and/or absorbed several times in the region of a strong radius of curvature, so that the intensity of the radiation is attenuated, and/or the radiation is reflected back into the interior of the housing.

Preferably, the first transport device and/or the second transport device is a pitch varying starwheel. This makes it possible to change the distance between two containers that follow one another directly on the transport path in the region of the first transport device and/or the second transport device. This makes it possible, for example, in the region of the second transport device, for the container to be guided past the container treatment device, e.g., a radiation emitter, at an individually adjustable speed. Thus, the treatment can be adapted to the required duration without having to adjust the speed of the entire carrier on which the holding device is arranged.

Likewise, by designing at least the first transport device and/or the second transport device as a pitch varying starwheel, it can be ensured that the transfer of a container from the first transport device to the second transport device is improved and runs with low losses, since the speed of the container to be transferred can be adjusted in the transfer region to a speed that is particularly suitable for the transfer. In particular, it is possible to synchronize the transfer speed by the pitch varying starwheel to the speed of a holding device of the other transport device in each case.

In a preferred embodiment, a drive device of the second transport device arranged within the housing is arranged outside the housing. In particular, this is a drive device which is arranged above the surface spanned by the transport path. This allows access to the drive device, e.g., for maintenance work, without having to open the housing.

Preferably, in addition to the second transport device, which is preferably associated with a container outer surface treatment device, a maximum of two further transport devices are arranged within the housing. As a result, the volume of the space enclosed by the housing can be reduced, and the container treatment apparatus can be designed to be particularly compact. In this embodiment, it is possible to deliver the containers after treatment by the container treatment apparatus to a treatment device following in the transport path in the same way as is the case with the treatment apparatuses known from the prior art having, for example, five transport devices. Due to the odd number of all transport devices within the space surrounded by the housing in this embodiment, the direction of rotation of the first and last transport devices along the transport path within the housing is identical.

Preferably, the housing encloses a clean room. This is in particular preferred if the container treatment apparatus is a sterilization device. In this way, at least a partial region within the housing can be kept sterile, and contamination of the containers sterilized within the housing can be avoided.

In addition or as an alternative, it is provided that the transport path along which the containers can be guided by the second transport device be arranged at least in portions within a clean room. This allows a surface sterilization during transport of the containers using the second transport device, without the risk of recontamination of the treated surface.

Preferably, the housing is a radiation barrier. If radiation is used to sterilize a container surface, the escape of this radiation or resulting scattered radiation from the housing can be prevented. This serves in particular to protect persons who are in the vicinity of such a container treatment apparatus.

Preferably, the radiation shielding device is directly adjacent to an opening in a housing designed as a radiation barrier. In this case, it is provided in particular that, between the housing and the radiation shielding device, no radiation be able to escape into the environment. In particular, it is therefore preferred that the radiation shielding device be directly adjacent to walls surrounding an opening in the housing.

Preferably, the transport path along which the containers can be guided by the second transport device runs at least in portions in a region of influence of a container outer surface treatment device for treating outer surfaces of the plastic containers, in particular a container outer surface sterilization device and/or a container inner surface treatment device for treating inner surfaces of the plastic containers, in particular a container inner surface sterilization device.

Preferably, a holding device of the second transport device (in particular if the second transport device is part of a container outer surface treatment device) is a holding device that grips the inside of the container, and/or (in particular if the second transport device is part of a container inner surface treatment device) a holding device of the container inner surface treatment device is a holding device that grips the outside of the container. These embodiments make it possible for the container to be held, at least on one container treatment device, on one side by a holding device on a container surface which is opposite the container surface to be treated. This means that no parts of the holding device have to come into contact with the container surface to be treated, so that said surface is freely accessible for the treatment to be carried out by the container treatment device. For example, it is thereby possible to apply the entire surface to be treated with a sterilization medium such as a sterilizing agent solution or sterilizing radiation.

In the following, a container is understood to mean any container that is suitable for holding a medium. Where reference is made to a first container and a second container, these may be identical or different. However, identical containers can have different contents. If the treatment apparatus is, for example, a filling apparatus, a first container can contain a gaseous medium, and the second container can contain a liquid or another gas. It would also be conceivable for the treatment apparatus to be a sterilization apparatus. In this case, for example, a first container could be a non-sterile container, and the second container a sterile container.

Preferably, the (first and/or second) container to be treated is a bottle and/or preform. The treatment apparatus is preferably a sterilization apparatus or a sterilization module. However, it would also be conceivable for the treatment apparatus to also have at least one treatment device which is selected from a group comprising a closing device, a blowing station, a filling device, a heating device, a cooling device, and a labeling device.

Preferably, the radiation shielding device extends from a transfer point or transfer region, at which containers can be transferred from a holding device of the first transport device to a holding device of the second transport device, in portions along the transport path on which the containers can be guided by the first transport device. Thus, a portion of the transport path is also surrounded by the radiation shielding device, which does not necessarily lie in the clean room.

Preferably, the radiation shielding device also extends along a direction in which the holding device of the first transport device is movable after the transfer of a container to a holding device of the second transport device. This allows particularly good shielding against the escape of radiation to be achieved. In this embodiment, the shielding is provided on both sides of the transfer region of the containers on the path that is covered by the holding element.

In particular preferably, the radiation shielding device extends along a circular arc on which the holding device of the first transport device can be guided. With this design of the radiation shielding device following a circular arc, it can be designed to be particularly compact.

Preferably, the radiation shielding device encloses a path on which a holding device of the first transport device is movable, at least in portions. In this case, in this portion of the first transport device, in particular a cross-section perpendicular to the transport direction is completely surrounded by the radiation shielding device. This provides particularly good shielding and therefore safety for the surroundings. In addition or alternatively, the radiation shielding device has a cross-section which essentially has the shape of the letter omega (Ω).

Preferably, the radiation shielding device is formed in at least two parts. In a preferred embodiment, the at least two radiation shielding device parts are separable from each other. This makes it possible to separate the parts of the radiation shielding device from one another—for example, to make an interior of the radiation shielding device accessible for maintenance work. In particular, it is preferred that the radiation shielding device parts be able to be spaced apart from one another by a drive.

In addition or as an alternative to this, the radiation shielding device has, in a first radiation shielding region which is arranged along the transport path upstream of a transfer point or transfer region at which containers can be transferred from a holding device of the first transport device to a holding device of the second transport device (hereafter also referred to as the preceding radiation shielding region), a larger cross-section in at least one direction arranged perpendicularly to the transport path than in a second radiation shielding region in which the holding device of the first transport device is movable after the transfer of a container to a holding device of the second transport device (hereafter also referred to as the subsequent radiation shielding region). This embodiment is particularly advantageous because the holding device of the first transport device downstream of the transfer point or transfer region is no longer equipped with a container and therefore takes up less space than upstream of the transfer point or transfer region. This allows the cross-section perpendicular to the transport path in the subsequent transfer region to be selected to be smaller. This in turn means that, in the case of a shorter length of the subsequent radiation shielding area, a similar number of reflections and absorptions of the radiation can occur as in the preceding radiation shielding region having a larger cross-section. Accordingly, a shielding performance of the subsequent radiation shielding region similar to that of the preceding radiation shielding region can be achieved even with a shorter length.

Preferably, the subsequent radiation shielding region has, at least in portions, a cross-section that widens starting from the transfer point or transfer region. This can prevent containers that are not correctly transferred to the second transport device from becoming wedged in the subsequent radiation shielding region and damaging a holding element.

Alternatively or in addition, it may be advantageous to provide regions, in the subsequent radiation shielding region, for ejecting and/or discharging containers that have been (not correctly) transferred to the second transport device.

Preferably, the radiation shielding device is not a clean room boundary, at least in portions. In this embodiment, the clean room boundary and the radiation shielding are thus separated from each other at least in portions, preferably in the region of the radiation shielding device. In particular, it is preferred that the radiation shielding device not form a clean room boundary at least in a region in which the radiation shielding device extends along a path on which a holding device of the first transport device is movable. The first transport device can therefore be designed to be non-sterile. This simplifies the accessibility and maintenance of the first transport device.

However, this is in particular advantageous if the treatment by the container outer surface treatment device and/or the container inner surface treatment device provides a height shift of the container. Specifically, in this case, it is not necessary for the container to be moved several times in height—for example, up and back down to its original position. Rather, it is conceivable that, during the treatment, the height shift take place only over the distance absolutely necessary for the process, and that the holding device be moved back to the height at which a further container is picked up only after the process has been completed and the treated container has been delivered. This makes it possible, in particular in the case of rotating container surface treatment devices, to carry out this displacement of the holding element, not occupied by a container, in a sector of a circular path in which no treatment of a container is carried out and which would therefore remain unused.

Preferably, a container holder or a holding device is a passive element—for example, a clamp. Active devices that are necessary for receiving and transferring, e.g., for pressing a preform into a clamp and pulling it out of a clamp against the holding force of the clamp, are preferably outsourced to the transfer device and the receiving device. In a preferred embodiment, a holding device of the container outer surface treatment device and/or the container inner surface treatment device is an active element. In the case of such an active element, the force with which a container is gripped can preferably be changed. For example, this change can occur depending upon the sector. This embodiment is preferred because the active holding elements/clamps ensure better and safer takeover and/or transfer.

Furthermore, the object underlying the invention is achieved by a method for transporting plastic containers, and in particular plastic preforms, along a predetermined transport path. In this case, the plastic containers are transported by several transport devices, wherein in each case at least one holding element holds a plastic container and guides this plastic container along a portion of the transport path. A plastic container is transferred from a holding device of a first transport device to a holding device of a second transport device. In particular, the method is characterized in that the containers are guided by the first transport device on a transport path which is arranged at least in portions outside a clean room, and the containers are guided by the first transport device on a transport path which is surrounded at least in portions by a radiation shielding device.

In a first variant of this method, the above-mentioned object is achieved in that a holding device of the second transport device is at least temporarily brought into the region of an opening of a housing wall in order to receive a container to be brought into the space surrounded by the housing. When transferred through this opening, the container is preferably surrounded at least in part by the radiation shielding device. As already described above with regard to the apparatus, this offers the possibility of keeping the volume enclosed by the housing small and at the same time ensuring efficient shielding of the environment against the radiation occurring in the housing.

This and all further solutions presented can be implemented in addition to or as an alternative to the first solution described above. The method steps and embodiments of the apparatus described in the context of preferred variants are also not limited to the solution in whose context they are first mentioned. Rather, preferred method steps and embodiments can also bring advantages for methods and/or apparatuses that have not been described in direct connection with this variant, provided that this combination is technically feasible.

Preferably, a longitudinal axis of a container, during its transport along the transport path, extends substantially perpendicular to a plane spanned by the transport path. The container thus extends in a height direction that is perpendicular to the transport path or the plane spanned by the transport path. Preferably, the perpendicular of the perpendicular projection of the transport path is parallel to the height of one, preferably each, container. The height direction above the perpendicular projection of the transport path is thus parallel to the height direction of the container(s).

Preferably, the longitudinal axis of a container during its transport along the transport path is substantially parallel to an axis of rotation of at least one carrier of the first and/or second transport device.

Preferably, at least one first and/or one second transport device has a plurality of holding elements, in particular holding clamps and/or mandrels or holding mandrels, for holding the plastic containers during transport. This makes it possible to transport a plurality of containers at the same time.

As explained above, in a preferred embodiment, the first transport device is a (first) pitch varying starwheel, and the second transport device is a (second) pitch varying starwheel. In this case, a pitch varying star is suitable and intended to change the separation of successive or adjacently transported plastic containers, and in particular to increase and/or reduce it. This is preferably achieved in that the holding elements of the first transport device and the holding elements of the second transport device are movably and/or pivotably mounted on the respective transport device/the respective pitch varying starwheel, and are pivotably mounted in particular radially or tangentially relative to the transport path of the respective transport device.

Pitch varying starwheels are therefore always used where divisions are to be varied or changed. If other functions are required, these are usually not carried out on the pitch varying starwheel, but additional transport starwheels or transport devices are required before and/or after the pitch varying starwheels. For example, in an apparatus known from the applicant's internal prior art, two transport starwheels are necessary, in order to hold the containers with holding mandrels for external treatment, and, downstream, a pitch varying starwheel, which is only provided for changing a division. Accordingly, pitch varying starwheels known from the prior art can only carry out movements horizontally, i.e., radially and/or tangentially to a plane—more precisely, a circumference—of the (pitch varying) starwheel, or in relation to a longitudinal direction of the plastic container, but not in other planes such as vertically, i.e., perpendicular to a plane of the (pitch varying) starwheel in relation to the circumference of the (pitch varying) starwheel or in relation to the longitudinal direction of the plastic container. Instead, these movements are usually carried out on other or additional transport units.

Preferably, a heating apparatus is arranged upstream of the container treatment apparatus, which heats the plastic containers and in particular plastic preforms to a predetermined temperature. The first transport device is advantageously arranged downstream of the heating apparatus, so that a transfer of the plastic containers from the heating apparatus to the container treatment apparatus, i.e., from an outlet starwheel (first transport device) of the heating apparatus to an inlet starwheel (second transport device) of the container treatment apparatus, is carried out with two pitch varying starwheels, without further transport starwheels or transport devices being arranged between these pitch varying starwheels.

The above-mentioned housing preferably has an enclosure within which a clean room is preferably formed. In this case, the first transport device is preferably arranged outside the housing and thus outside the clean room, and the second transport device is preferably arranged inside the housing and in particular inside the clean room. The first transport device therefore preferably transfers the plastic containers to the second transport device, which is arranged within a housing that shields the environment. The second transport device or the second pitch varying starwheel is therefore preferably designed to be aseptic.

The first transport device or the pitch varying starwheel arranged downstream of the heating device therefore preferably transfers the plastic containers directly to a further pitch varying starwheel, on which an external treatment of plastic containers is also carried out directly. In the prior art, an inlet starwheel is usually initially provided after the first pitch varying starwheel within the housing, which inlet starwheel transfers the containers to the subsequent transport starwheel for external disinfection, which in turn transfers the containers to the second pitch varying starwheel after external treatment.

Due to the container treatment apparatus according to the invention or the proposed transfer from a pitch varying starwheel to a directly subsequent pitch varying starwheel, on which the external treatment is also carried out, the inlet starwheel arranged in the housing, and the treatment transport starwheel, are therefore eliminated, so that the housing can in particular also be made smaller overall. The necessary radiation shielding can be ensured by the radiation shielding device, which is preferably separated from the clean room boundary and arranged in the region of the first transport device.

The transfer of a container from the first to the second transport device preferably takes place in the region of a transfer window, which is arranged in a housing which also forms a clean room boundary. In the region of this transfer window, the separation of the plastic containers is preferably variable, so that the pitch delay of the first pitch varying starwheel is optimally designed for or adjustable to the requirements of the second pitch varying starwheel.

In a preferred embodiment, the transfer window has a width which is between 250 mm and 320 mm, preferably between 270 mm and 310 mm, and particularly preferably between 285 mm and 300 mm. Advantageously, the transfer window is designed to be as small as possible so that any sterility inside the housing can be maintained, and, at the same time, the exit window for possible radiation escaping from the housing is reduced. Preferably, the transfer window is designed to be variable so that its width can be changed. This is advantageous, for example, because the transfer window can be adapted to different preform types and sizes.

In a further preferred embodiment, the second transport device has a lifting and rotating device which enables a movement of the holding element of the second transport device in a vertical and/or horizontal direction with respect to a longitudinal axis of the plastic container, and a rotational movement of the plastic container and/or the holding element along the longitudinal axis. Preferably, each holding element of the second transport device is assigned its own lifting and rotating device so that the plastic containers can be rotated independently of one another, and/or the holding elements can be moved independently of one another. Each lifting and rotating device is preferably assigned a drive device, which is designed in a known manner, in particular for carrying out the rotational movement of the plastic container. The lifting movement of the holding element in the vertical direction is preferably realized by one or more lifting curves and at least one guide curve.

In order to enable the transfer from the first transport device to the second transport device and in particular from the first pitch varying starwheel to the second pitch varying starwheel, a lifting and rotating device is accordingly additionally arranged on the second transport device/the second pitch varying starwheel, which is preferably suitable and intended for receiving the plastic containers.

In this case, the lifting and rotating device is required in order to be able to pick up the plastic containers and hold them on the inside, wherein the transfer from the holding elements and in particular holding clamps of the first transport device to the holding elements and in particular holding mandrels of the second transport device preferably takes place by a movement of the holding elements of the second transport device towards the containers, and therefore preferably in the vertical direction or in the longitudinal direction of the containers, so that the holding element is moved in the direction of the container. In addition, the lifting and rotating device serves to rotate the containers in front of the container outer surface treatment device, and in particular the container outer surface sterilization device, about their longitudinal axis, so that a radiation power evenly distributed around the circumference, and thus a resulting uniform disinfection performance, can be applied to the containers.

In this case, the holding elements of the first transport device are preferably holding clamps which hold the plastic containers on an outer wall and in particular below or above the support ring of the containers. The holding elements of the second transport device are preferably holding mandrels which are inserted into the containers and hold them on an inner wall. The plastic containers are therefore preferably transferred from an external holding element to an internal holding element, and in particular from an external holding clamp to an internal holding mandrel.

Preferably, a portion of the housing and in particular an upper portion of the housing is arranged to be stationary, and a further portion, in particular a lower portion, which is a bottom, is arranged to be movable and in particular lowerable. The lower portion is preferably—as is the case with the upper portion—a shielding device, such as, in particular, a radiation protection wall. In this case, the arrangement of the two shielding devices is designed such that the lifting and rotating device and in particular at least one guide roller of the lifting and rotating device can move on a track through a gap between the two shielding devices.

The radiation protection walls of the housing and/or the radiation shielding device are advantageously made of a special radiation-shielding material—for example, lead encased in stainless steel, or tungsten, or a tungsten sintered composite, or a material having similar properties.

Nevertheless, parts of the radiation shielding device are preferably also made of stainless steel or cast material. Adapting the shielding material to improved radiation sealing results in a significantly lower wall thickness of the shielding and thus the possibility of moving with the lifting-rotating unit between the two protective walls on the track of the pitch varying starwheel, or of allowing the shielding to protrude into the lifting-rotating device without having to widen or enlarge it unduly.

The shape of the radiation shielding device preferably follows the path of a holding element of the first transport device. This means that it can be made particularly small and with little material expenditure, while maintaining the same shielding performance.

In a further preferred embodiment, at least one wall of the radiation shielding device runs parallel to a portion of the transport path of the containers. This design allows the overall size of the radiation shielding device to be reduced. In particular, the radiation shielding device is a radiation shielding device that is toroidal in shape, at least in portions, along the transport path of the plastic preforms.

Further advantages and embodiments result from the accompanying drawings.

DETAILED DESCRIPTION OF THE INVENTION

Figure 1:
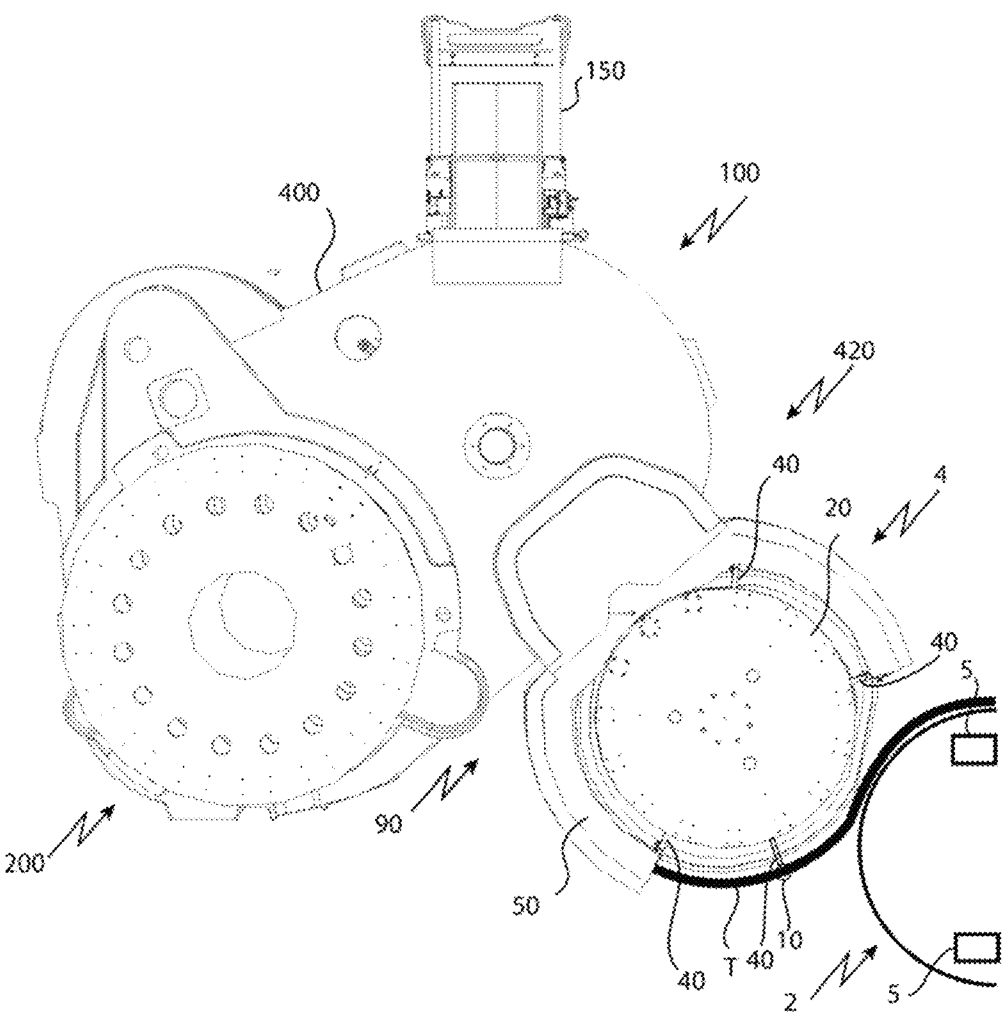
FIG. 1 shows a schematic plan view of a container treatment apparatus in an exemplary embodiment.

FIG. 1 shows a schematic plan view of a container treatment apparatus 1 in an embodiment by way of example. The container treatment apparatus 1 shown, which, in the example shown, is a container sterilization apparatus, has three transport devices 100, 200, 300 for transporting a container 10 along a transport path T, not highlighted in this illustration, within a housing 400. Since the transport devices 100, 200, 300 guide the containers 10 inside the housing 400 that forms a clean room, the transport devices 100, 200, 300 and the containers 10 are not shown in this illustration, or are shown only in portions.

One of the transport devices 100, 200, 300 is a container outer surface treatment device 100, of which a container outer surface application device 150 or a radiation source 150 is arranged as an externally accessible attachment part on the housing 400. Of a container inner surface treatment device 200, only parts located outside the housing 400 are visible. These can, for example, be parts of a lifting mechanism 280, by which a container inner surface application device 250 (not shown here), e.g., a radiation finger 250, can be moved in a relative manner with respect to a container 10. The transport devices 100 and 200 each have a plurality of holding devices 140, 240 for holding at least one container 10 during container treatment and/or transport along the transport path T.

In the embodiment shown, the transport device 4 is arranged downstream of a heating apparatus 2 (shown only schematically), which comprises at least one heating device 5 such as an oven or a (for example, infrared or microwave) radiation source 5. The transport device 4 has a plurality of holding elements 40 for receiving the containers 10, which are arranged together on a rotatable carrier 20.

In the exemplary embodiment shown, the transport device 4 is arranged outside the housing 400. Only the holding elements 40 penetrate into the housing interior, in portions, through an opening 420 of the housing 400, in order to transfer the containers 10.

Even though the transport device 4 is arranged outside the housing 400 in the exemplary embodiment shown, the holding elements 40 and the containers 10 arranged thereon are not or only partially visible, since they are guided at least in portions in a radiation shielding device 50. In this exemplary embodiment, the radiation shielding device 50 extends in portions along the transport path T along which the containers 10 are guided.

In addition, the radiation shielding device 50 also extends into the region of the opening 420 of the housing 400. As a result, it can effectively shield both the radiation emerging in the region of the opening 420 of the housing 400 and radiation propagating along the path over which the holding elements 40 of the transport device 4 are guided.

As a further treatment of the containers following the treatment in the container treatment apparatus 1, their forming, for example, into other containers 10, such as bottles, can be carried out by a forming device (not shown). In addition or as an alternative, it would be conceivable to fill (and, if necessary, close) the containers 10 treated by the container treatment apparatus 1.

Figures 2, 3:
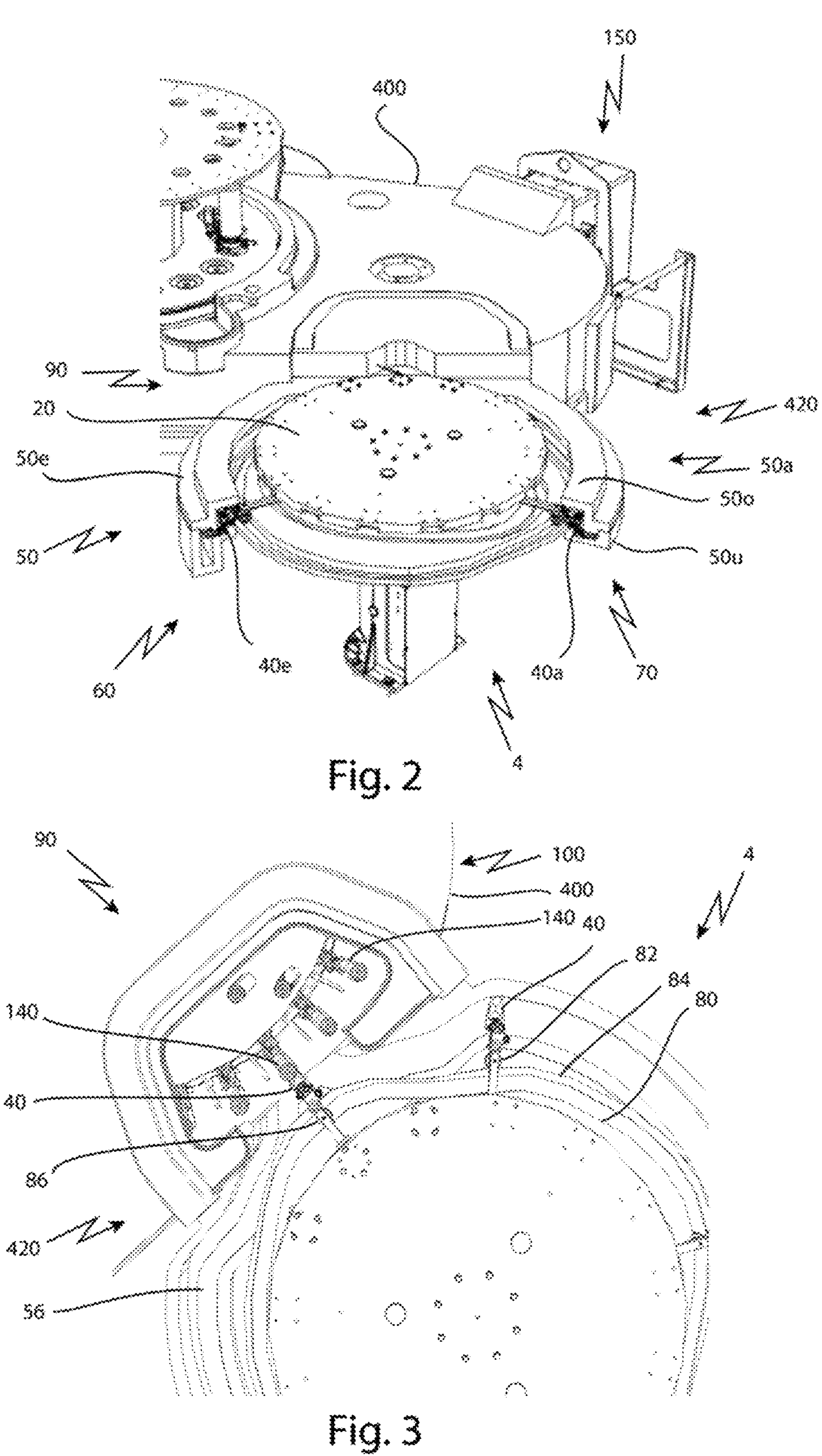
FIG. 2 shows a perspectival view of the embodiment shown in FIG. 1, obliquely from above.
FIG. 3 shows a plan view of the transfer region without the upper part of the radiation shielding device.

FIG. 2 shows a cutout of the embodiment of the container treatment apparatus 1 shown in FIG. 1, in a perspectival view obliquely from above. In the foreground, the transport device 4 is visible. The heating apparatus 2, located downstream with respect to this, is not shown.

The transport device 4 has a plurality of holding elements 40 for receiving the containers 10, of which one holding element 40*e* is arranged in the region of the inlet 60 of the radiation shielding device 50, and another holding element 40*a* is arranged in the region of the outlet 70 of the radiation shielding device 50. A container 10 is not arranged in either of these two holding elements 40*a* and 40*e*, but, in normal operation, the holding element 40*e* arranged in the region of the inlet 60 of the radiation shielding device 50 would be equipped with a container 10.

In order to be able to guide a container 10 along the transport path T surrounded by the radiation shielding device 50 in this portion, the radiation shielding device 50 is designed in the form of a channel in the portion 50*e* between the inlet 60 and the transfer region 90, which is located in the region of the opening 420 in the housing 400, such that a container can be guided therein. For this purpose, the radiation shielding device 50 has a channel 56 in the portion 50*e*, which channel extends along a portion of the transport path T and in which the containers can be guided along the transport path T.

Since containers are not usually guided in the portion 50*a* between the transfer region 90 and the outlet 70, there is no channel in this region through which containers could be guided. The channel formed by the radiation shielding device 50 has a smaller cross-section in this portion 50*a* than in portion 50*e*. However, the channel is also wide enough in the portion 50*a* so that the holding elements 40 can be passed through and thus can follow the rotation of the rotatable carrier 20. The terms holding element and holding device are used synonymously in the context of this description.

Furthermore, it can be seen that the radiation shielding device 50 is formed in two parts and comprises an upper radiation shielding device part 50*o* and a lower radiation shielding device part 50*u*. This multi-part design makes it possible to open the radiation shielding device 50 by moving the two radiation shielding device parts 50*o* and 50*u* apart—for example, for cleaning or maintenance purposes.

The embodiments of the inlet 60 of the radiation shielding device 50 and of the outlet 70 of the radiation shielding device 50 are shown and described in more detail in connection with FIGS. 6 and 7.

FIG. 3 shows a plan view of the transfer region 90 without the upper part 50*o* of the radiation shielding device 50. In a state as shown in FIG. 3, the upper radiation shielding device part 50*o* of the radiation shielding device 50 is removed from the lower radiation shielding device part 50*u*, so that the region located within the radiation shielding device 50, such as the channel 56, becomes accessible—for example, for cleaning or maintenance work.

In this state, the holding elements 40 can also be seen. In particular, the transfer region 90 can also be seen, which extends into an opening 420 in the housing wall. In this transfer region 90, the containers 10 are transferred from a holding element 40 of the first transport device 4 to a holding device 140 of the second transport device 100. In the open state shown, there is access to the transfer region 90, and it is comparatively easy to set the holding elements 40 of the first transport device 4 and the holding devices 140 of the second transport device 100 and to adjust them in such a way that a safe transfer of the containers 10 is ensured.

The transfer region 90 preferably also represents a clean room boundary. Regions outside the housing 400 are typically not sterilized. The penetration of contamination into the clean room can be prevented, for example, by an overpressure inside the housing 400. Due to this overpressure, there is a continuous gas flow from the interior of the housing 400, through the opening 420, to the outside, so that contamination against this gas flow is possible only to a very limited extent. Although the containers 10 introduced into the clean room in the transfer region 90 are not sterile, they are brought by the second transport device, immediately after introduction, into the effective region of the radiation source 150 (not shown here) and sterilized there. The containers come into contact beforehand only with the associated holding device 140, which is also guided past the radiation source 150 and is also sterilized. The risk of contamination is therefore extremely low.

In addition, control cams 70, 80 can be seen in FIG. 3, by which the holding elements 40 can be controlled in a relative manner with respect to the rotatable carrier 20. For this purpose, guide rollers 82, 86 are each arranged on a control cam 80, 84. These guide rollers 82, 86 roll on the respective control cam 80, 84 during rotation of the rotatable carrier, and move a mechanism connected to the guide rollers 82, 86 according to the radial distance of the guide roller 82, 86 from the axis of rotation. This allows movements of the holding elements 40 to be actuated depending upon the sector that this holding element 40 is currently covering during rotation. This makes it possible for each holding element 40 to make exactly one predetermined movement at a certain position on the circular path. This movement can also be a combination of several movements which are specified by different control cams 80, 84. For example, a first control cam 70 could control a movement of the holding element 40 in the radial direction, whereas another control cam specifies a relative movement of the holding element 40 with respect to the rotatable carrier 20 along the circumferential direction. Likewise, the opening and closing of a holding device 40 for holding a container, or a lifting movement of the holding device 40 along the longitudinal direction of the container, could be controlled by a guide curve.

Of particular importance in this context are shapes in the control cam 80, by which a radial distance of a holding device 40 with respect to the axis of rotation of the rotatable carrier 20 can be controlled. In the embodiment shown, the control cam 80 is shaped such that a holding element 40 is displaced radially inwards both before and after reaching the transfer region 90. Only immediately before and after the arrangement of the holding element 40 in the transfer region 90 the holding element 40 is displaced radially outwards. Due to this design, the path covered by the holding element 40 before and after the transfer region 90 changes its radius of curvature several times.

The change in the radius of curvature can include a change from a strong radius of curvature to a small radius of curvature (with the same sign and thus the same direction of curvature), and vice versa. In particular, however, it is preferred that the radius of curvature change its sign (i.e., the direction of curvature) at least once. The channel 56 preferably follows this curvature, and has a corresponding change in its radius of curvature.

By changing the radius of curvature, it can be ensured that the radiation shielding device 50 nevertheless effectively prevents radiation incident along the course of the channel from escaping into the environment, since, in regions having a particularly strong radius of curvature, a particularly effective reflection and/or absorption of the radiation takes place. The radiation shielding device 50 forms a radiation trap by changing the radius of curvature and/or the direction of curvature (if necessary, several times). Preferably, the radiation is reflected and/or absorbed several times in this region, so that the intensity of the radiation is attenuated, and/or the radiation is reflected back into the interior of the housing.

Figure 4:
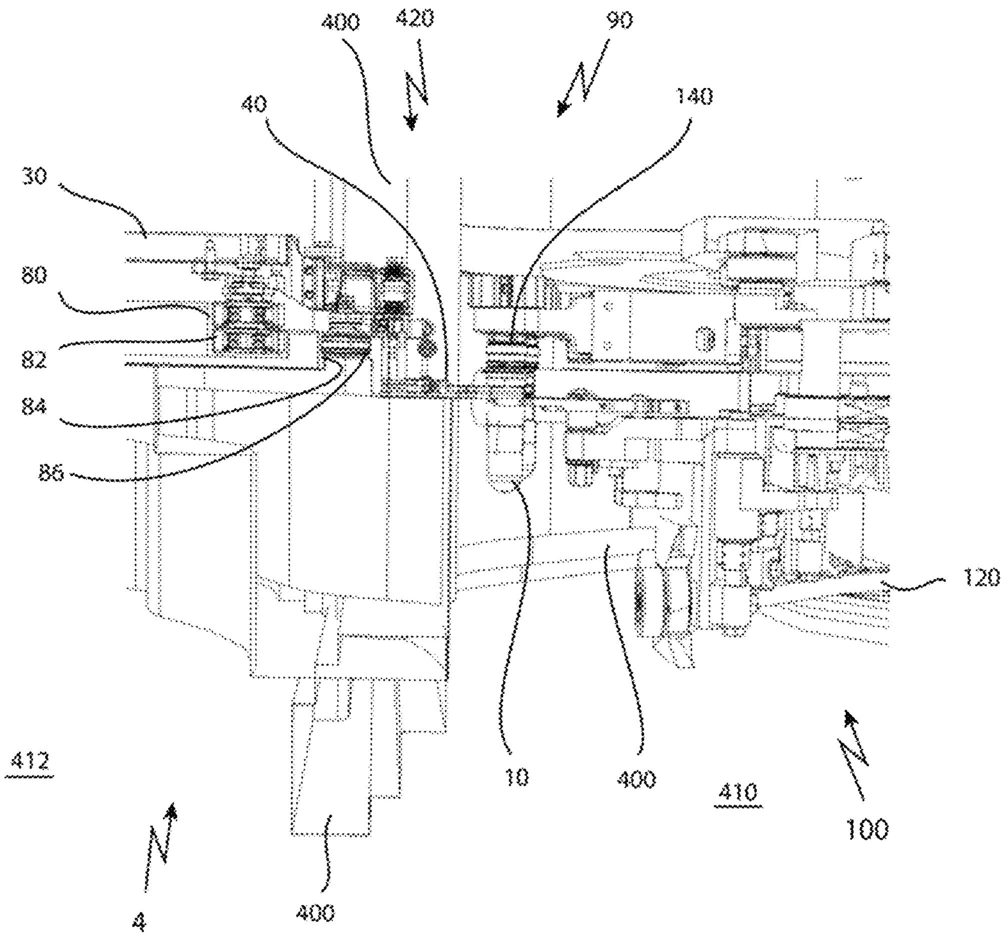
FIG. 4 shows a sectional view of the container treatment apparatus in the container transfer region.

FIG. 4 shows a sectional view of the container treatment apparatus 1 in the region of the container transfer 90.

On the left, a portion of the first transport device 4 is shown. Thus, an arm 30 is shown, to which a holding element 40 is attached. This arm 30 can be moved in a relative manner with respect to the rotatable carrier 20 via the guide rollers 82 and 86 that roll on the control cams 80 and 84. For example, it is possible to push the holding device 40 in the region of the opening 420 in the housing wall 400 radially outwards in the direction of a holding device 140 of the second transport device 100.

In the transfer region 90, a container 10 is shown, which is contacted by two holding devices 40, 140. This container 10 is, consequently, just transferred from the holding device 40 of the first transport device 4 to a holding device 140 of the second transport device 100. After the holding device 140 of the second transport device 100 has securely grasped the container, the holding device 40 of the first transport device 4 can release the container and, for example, be retracted radially inwards with respect to the rotatable carrier 20. This can be done, for example, by one of the control cams 80, 84.

The container can then be moved further on the holding device 140 of the second transport device 100—for example, by rotating the rotatable carrier 120 on which the holding device 140 is arranged.

By such a transfer from the first transport device 4 to the second transport device 100, it is possible to introduce a container through the opening 420 in the housing wall 400 from a non-sterile outdoor region 412 into the clean room 410.

At least one holding device 140 of the container outer surface treatment device 100 can be brought at least temporarily into the region of an opening 420 of the housing wall 400. This makes it possible for this holding element 140 to receive a container from a space 412 outside the housing 400 from a transport device 4 arranged there upstream with respect to the transport path. This design eliminates the need for an additional transport device within the housing, which picks up the container from outside and passes it on to the container outer surface treatment device 100.

Figure 5:
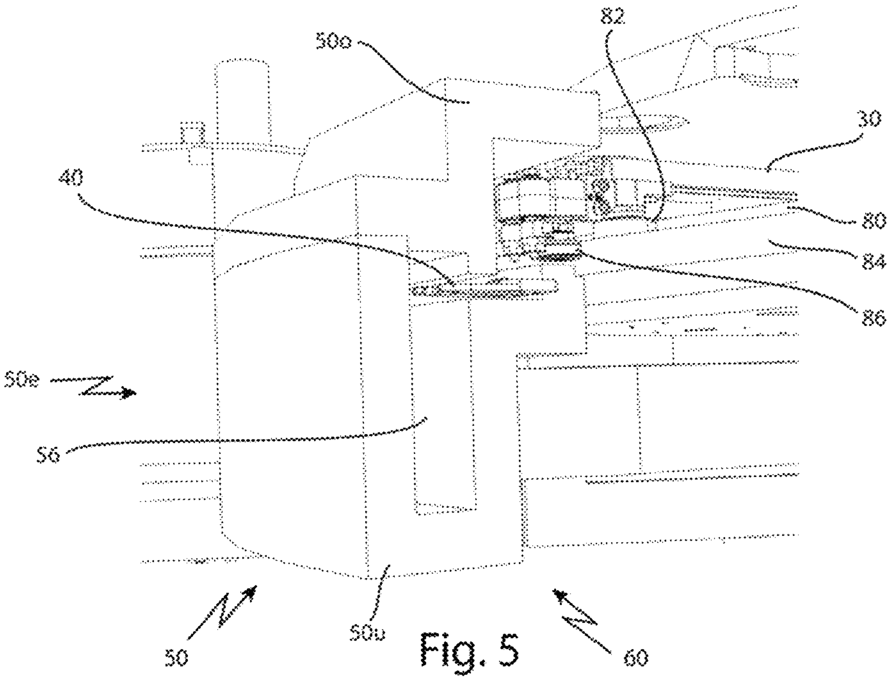
FIG. 5 shows a sectional view of the inlet into the radiation shielding device.

FIG. 5 shows a sectional view of the inlet 60 into the radiation shielding device 50. The inlet 60 is followed along the transport path T by the portion 50*e* of the radiation shielding device 50 between the inlet 60 and the transfer region 90. In this region, the radiation shielding device 50 is formed in at least two parts and comprises an upper radiation shielding device part 50*o* and a lower radiation shielding device part 50*u*. Together, these radiation shielding device parts 50*u* and 50*o* form a casing of the transport path, which encloses it in a vertical cross-sectional direction in such a way that radiation cannot escape directly. If radiation could escape at all, this would only be possible after repeated reflection on the inner surfaces of the radiation shielding device 50 and the associated loss of energy.

Between the two radiation shielding device parts 50*u* and 50*o* there is preferably on the radially inner side a gap through which parts of the holding device 40 can be passed. Thus, the holding device 40 can be connected to the rotatable carrier via an arm 30, and, nonetheless, the container 10 (not shown) can be guided inside the channel 56 formed by the radiation shielding device 50.

In FIG. 5, the control cams 80 and 84 are also clearly visible, which can control the holding element 40 by interacting with the guide rollers 82 or 86.

Figure 6:
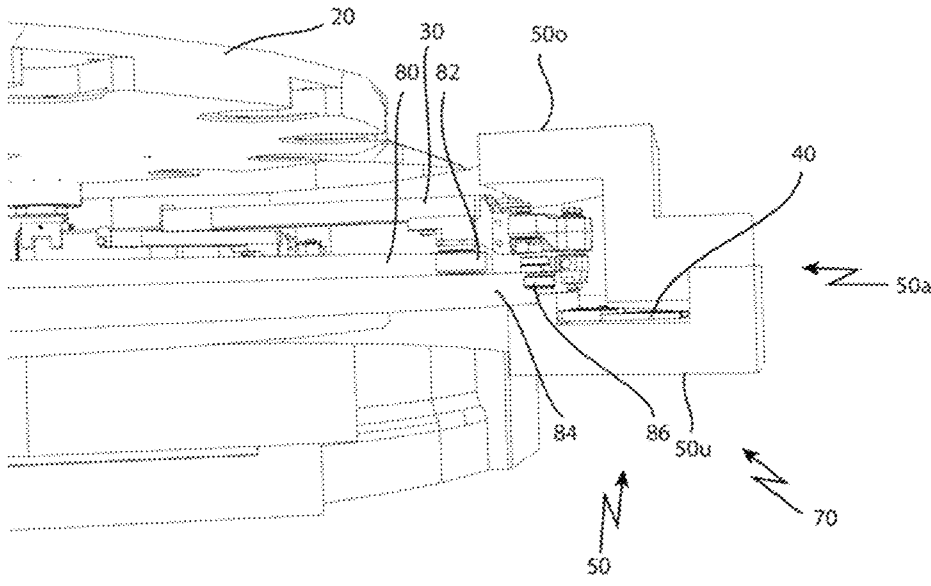
FIG. 6 shows a sectional view of the outlet from the radiation shielding device.

FIG. 6 shows a sectional view of the outlet 70 from the radiation shielding device 50. The outlet 70 closes off the portion 50*a* of the radiation shielding device 50 along the transport path T, which is arranged between the transfer region 90 and the outlet 70. In this portion, the radiation shielding device 50 is preferably also designed in at least two parts and comprises an upper radiation shielding device part 50*o* and a lower radiation shielding device part 50*u*. However, in this portion 50*a*, containers are usually not guided through the radiation shielding device 50, thus, the formation of a comparatively large channel is not necessary. Rather, the region between the upper radiation shielding device part 50*o* and the lower radiation shielding device part 50*u* can be so narrow that only the holding device 40 can be guided between these two radiation shielding device parts 50*o* and 50*u*.

Due to the small space between the two radiation shielding device parts 50*u* and 50*o*, the escape of radiation is particularly well inhibited. If radiation could escape at all, this would only be possible after repeated reflection on the inner surfaces of the radiation shielding device 50 and the associated loss of energy. The number of reflections and thus also the energy loss is significantly increased due to the significantly smaller free distance between the inner walls of the radiation shielding device 50, compared to the portion 50*e*. The escape of high-energy radiation can thus be effectively prevented.

As also in FIG. 5, the control cams 80 and 84 are also clearly visible in FIG. 6, which cams can control the holding element 40 by interacting with the guide rollers 82 or 86.

Figure 7:
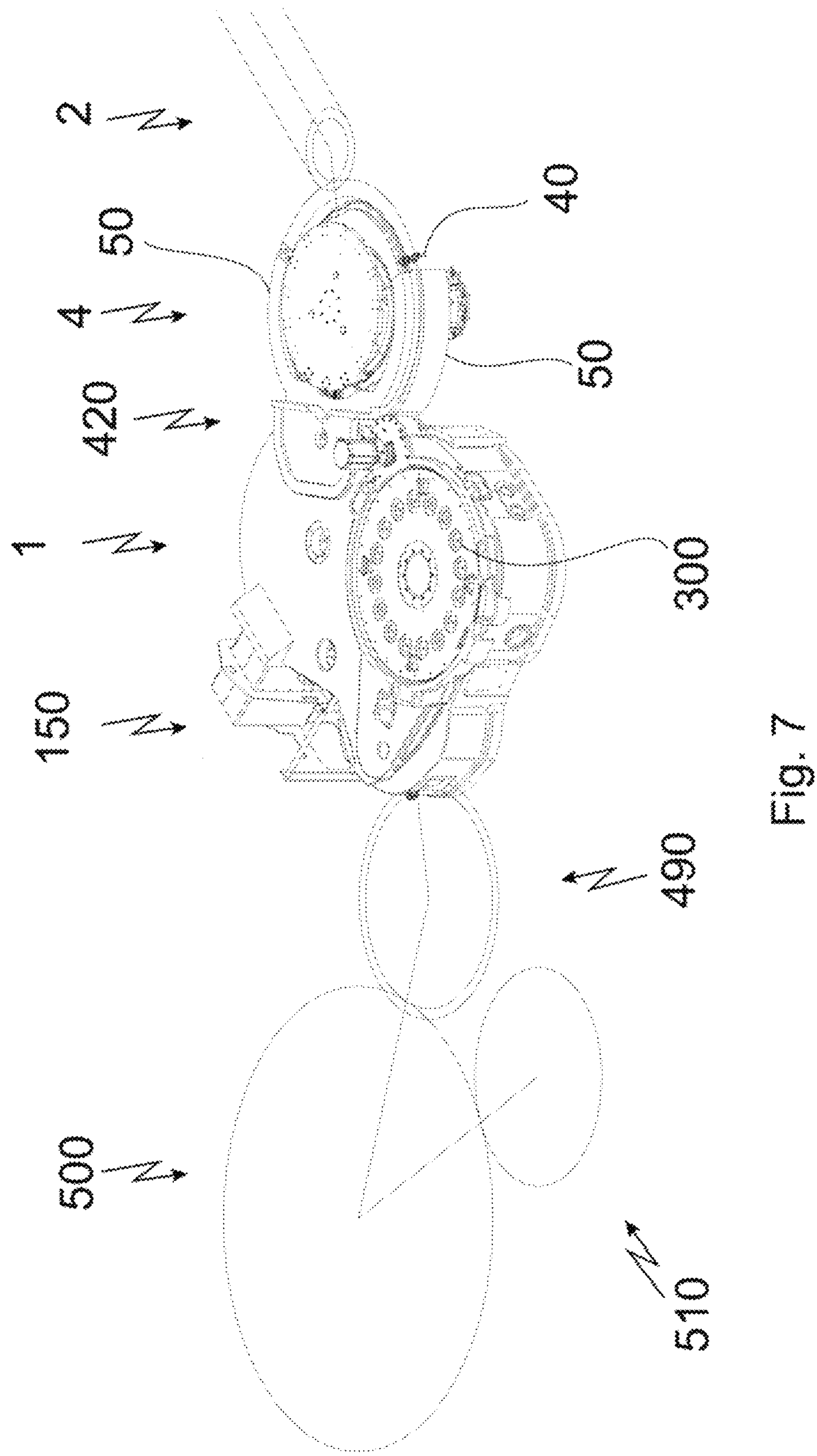
FIG. 7 shows a schematic, oblique plan view of a container treatment apparatus having upstream and downstream container treatment devices.

FIG. 7 shows a schematic oblique view of a container treatment apparatus 1 having upstream and downstream container treatment devices 2, 500. In the example shown, the container treatment devices 2, 500 illustrated are, on the one hand, a heating apparatus 2 which is arranged upstream of the first transport device 4 and, on the other hand, a container-forming device 500. In the container-forming device 500, for example, preforms are formed into bottles, preferably by blow molding. An inlet starwheel 490 is arranged upstream of the container forming device 500 and an outlet starwheel 510 downstream.

In the example shown, the container treatment apparatus 1 is a sterilization device in which the containers are applied with sterilizing radiation from the radiation source 150. Likewise, in the container treatment apparatus 1, an internal container sterilization is provided in the region of the transport device 300. However, at least some of the necessary devices are not shown in FIG. 7.

The radiation shielding device 50 is shown in FIG. 7 in a closed state. The upper radiation shielding device part 50*o* thus rests on the lower radiation shielding device part 50*u*, so that a flush barrier for radiation emerging from the transfer region is created.

In the embodiment shown in FIG. 7, an opening 58 is provided in the upper radiation shielding device part 50*o*, through which a fluid can be guided into the transfer region 90. The opening can therefore also be referred to as a fluid connection. By supplying a (preferably sterile) fluid into the transfer region, an overpressure can be generated locally there, which causes the fluid, preferably a gas, to flow out of the housing 400 through the opening 420. This can effectively prevent contaminants from flowing in against this fluid flow. However, this does not significantly hinder the insertion of the containers into the interior of the housing.

Figure 8:
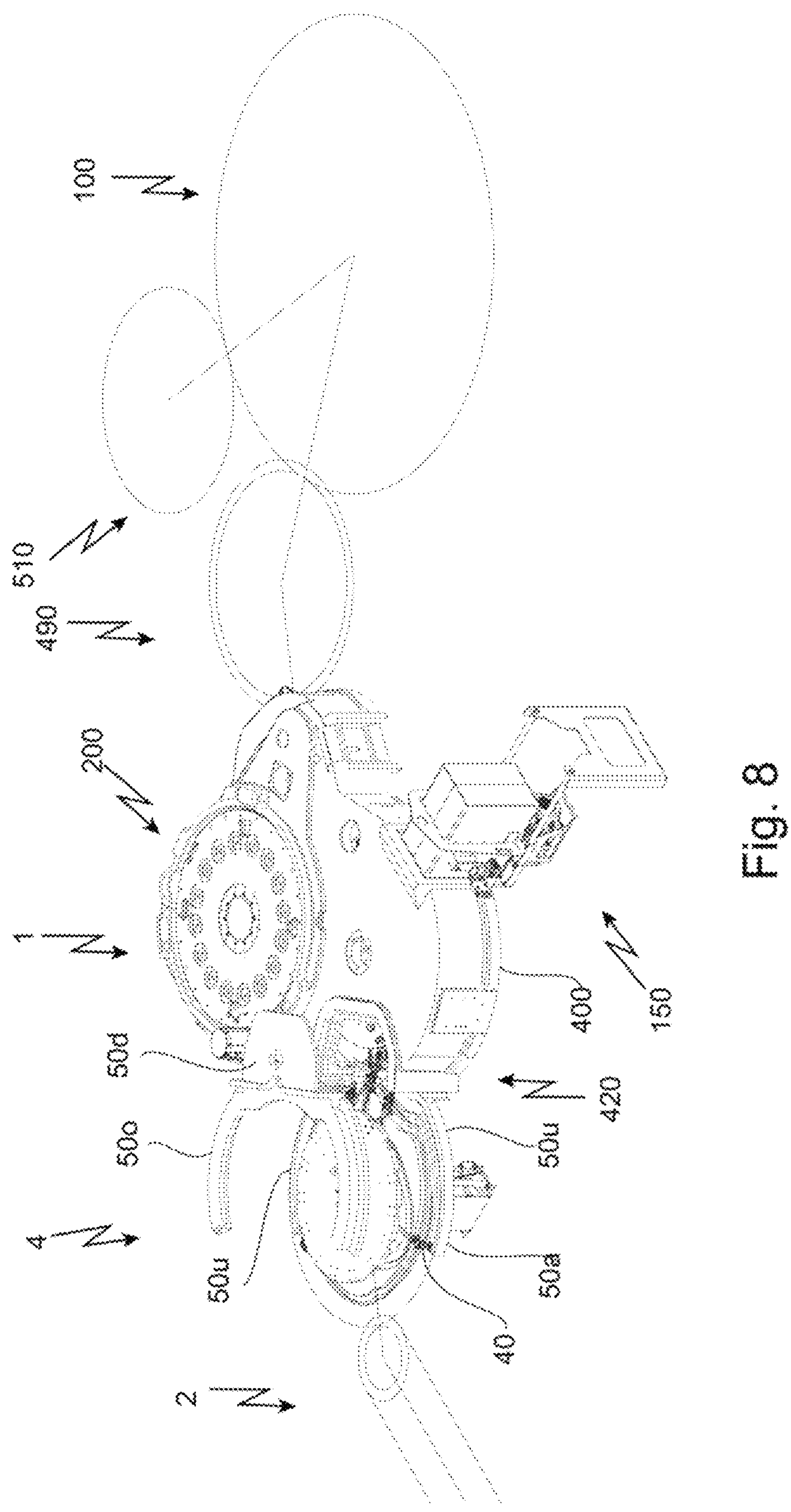
FIG. 8 shows a further schematic, oblique plan view of a container treatment apparatus having upstream and downstream container treatment devices, in a state with the radiation shielding device open.

FIG. 8 shows a further schematic oblique view of a container treatment apparatus having upstream and downstream container treatment devices, in a state with the radiation shielding device 50 open.

The container treatment devices 2, 500 shown in FIG. 8 upstream and downstream of the container treatment apparatus 1 correspond to those shown in FIG. 7. These are thus a heating apparatus 2 arranged upstream of the first transport device 4, and a container-forming device 500 arranged downstream of the container treatment apparatus 1. Here, too, an inlet starwheel 490 is arranged upstream of the container forming device and an outlet starwheel 510 downstream.

The container treatment apparatus 1 is in turn a sterilization device, having a container outer sterilization by the radiation source 150 and a container inner sterilization in the region of the transport device 300.

The radiation shielding device 50 is shown in FIG. 8 in an opened state in which the upper radiation shielding device part 50*o* has been removed upwards from the lower radiation shielding device part 50*u*. This makes the space formed between these two radiation shielding device parts 50*o* and 50*u* accessible—for example, for cleaning or maintenance work.

In particular, however, the transfer region is accessible in this state. This makes it relatively easy to perform maintenance in this region and/or to correctly adjust the transfer of containers. The transfer region has proven to be particularly critical, which is why a particularly precise adjustment of the transfer is necessary, in particular the coordination of the movement of the holding elements 40 of the first transport device 4 and the holding elements 140 of the second transport device 100—if necessary, taking into account the geometry of the containers to be transferred.

In a particularly preferred embodiment, the upper radiation shielding device part 50*o* is formed in at least two parts. In particular, it is preferred that a part 50*d* of the upper radiation shielding device part 50*o*, which is preferably at least in portions a cover of the opening 420 in the housing 400, be separately movable. This makes it possible for the particularly critical region in the transfer region to be made separately accessible or not. For example, it may be advantageous to leave this region covered if, for example, maintenance is necessary due to a container—located in the portion 50*a* of the radiation shielding device 50 between the transfer region 90 and the outlet 70—that has not been correctly transferred. In addition, a separate opening of the part 50*d* of the upper radiation shielding device part 50*o* can be useful if, for example, maintenance or adjustment is necessary in the region of the transfer 90, and contamination of the channel between the upper and lower radiation shielding device parts 50*o* and 50*u* is to be avoided.

The applicant reserves the right to claim all features disclosed in the application documents as essential to the invention, provided that they are novel over the prior art individually or in combination. It is also pointed out that features which can be advantageous in themselves are also described in the individual figures. The person skilled in the art will immediately recognize that a particular feature described in a figure can be advantageous even without the adoption of further features from this figure. Furthermore, the person skilled in the art will recognize that advantages can also result from a combination of several features shown in individual or in different figures.

LIST OF REFERENCE SIGNS

1 container treatment apparatus
2 heating apparatus
4 first transport device, transport starwheel (outside the housing)
5 heating device
6 drive device of the transport device or of the transport starwheel 4
10 container, preform
11 mouth of the plastic preform
14 support ring
20 rotatable carrier
30 arm
40 holding element
50 radiation shielding device
50*o* upper radiation shielding device part
50*u* lower radiation shielding device part
50*e* portion of the radiation shielding device between the inlet and the transfer region
50*a* portion of the radiation shielding device between the transfer region and the outlet
58 opening, fluid connection
60 inlet
70 outlet
80 control cam
82 guide roll
84 control cam
86 guide roll
90 transfer region, container transfer region
100 container outer surface treatment device, second transport device
105 lifting and rotating device
110 shifting device, shifting mechanism
120 rotatable carrier
132 rotor of the lifting and rotating device
140 holding element, holding device, mandrel
150 container outer surface treatment device, radiation source
200 container inner surface treatment device, transport device
300 transport device, transport starwheel (inside the housing)
400 housing
410 space inside the housing, housing interior, clean room
412 space outside the housing, environment
420 window, opening (for loading into the housing interior)
490 inlet starwheel
500 blow molding device
510 outlet starwheel
T transport path

The invention claimed is:

1. A container treatment apparatus for transporting plastic containers along a predetermined transport path, wherein the container treatment apparatus has several transport devices, each of which has at least one holding element configured for holding a plastic container and guiding the plastic container on a portion of the transport path, wherein a second transport device immediately follows a first transport device along the transport path, and containers can be transferred from a holding device of the first transport device to a holding device of the second transport device, wherein the transport path along which the containers can be guided by the first transport device is arranged at least in portions outside a clean room, and the transport path along which the containers can be guided by the first transport device is surrounded at least in portions by a radiation shielding device, and wherein the radiation shielding device is not a clean room boundary.

2. The container treatment apparatus according to claim 1, wherein the transport path along which the containers can be guided by the second transport device is arranged within a clean room, at least in portions.

3. The container treatment apparatus according to claim 1, wherein the first transport device and/or the second transport device is a pitch varying starwheel.

4. The container treatment apparatus according to claim 1, wherein the transport path along which the containers can be guided by the second transport device extends at least in portions in a region of influence of a container outer surface treatment device for treating outer surfaces of the plastic containers.

5. The container treatment apparatus according to claim 1, wherein the radiation shielding device extends, proceeding from a transfer point or transfer region at which containers can be transferred from a holding device of the first transport device to a holding device of the second transport device, in portions along the transport path on which the containers can be guided by the first transport device.

6. The container treatment apparatus according to claim 1, wherein the radiation shielding device encloses, at least in portions, a path on which a holding device of the first transport device is movable, and/or the radiation shielding device has a cross-section which essentially has the shape of the letter omega.

7. The container treatment apparatus according to claim 1, wherein the radiation shielding device is designed in at least two parts.

8. The container treatment apparatus according to claim 1, wherein the radiation shielding device, in a first radiation shielding region which is arranged along the transport path upstream of a transfer point or transfer region at which containers can be transferred from a holding device of the first transport device to a holding device of the second transport device, has a larger cross-section in at least one direction arranged perpendicularly to the transport path than in a second radiation shielding region in which the holding device of the first transport device is movable after the transfer of a container to a holding device of the second transport device.

9. The container treatment apparatus according to claim 1, wherein a path on which a holding element of the first transport device can be guided changes its radius of curvature at least once, wherein this change in the radius of curvature includes a change from a large radius of curvature to a small radius of curvature and vice versa, and/or includes at least a one-time change in a direction of the radius of curvature.

10. A method for transporting plastic containers along a predetermined transport path, wherein the plastic containers are transported by several transport devices, wherein in each case at least one holding element holds a plastic container and guides said plastic container along a portion of the transport path, wherein a plastic container is transferred from a holding device of a first transport device to a holding device of a second transport device, wherein the containers are guided by the first transport device on a transport path which is arranged at least in portions outside a clean room, and the containers are guided by the first transport device on a transport path which is surrounded at least in part by a radiation shielding device, and wherein the radiation shielding device is not a clean room boundary.

11. The container treatment apparatus according to claim 1, wherein the radiation shielding device extends, proceeding from a transfer point or transfer region at which containers can be transferred from a holding device of the first transport device to a holding device of the second transport device, in portions along the transport path on which the containers can be guided by the first transport device, and also along a direction in which the holding device of the first transport device can be moved after the transfer of a container to a holding device of the second transport device.

12. The container treatment apparatus according to claim 1, wherein the radiation shielding device has a cross-section which essentially has the shape of the letter omega.

13. The container treatment apparatus according to claim 7, wherein the at least two radiation shielding device parts are separable from one another.

14. The container treatment apparatus according to claim 1, wherein the radiation shielding device does not form a clean room boundary, at least in a region in which the radiation shielding device extends along a path on which a holding device of the first transport device is movable.

15. The container treatment apparatus according to claim 1, wherein the radiation shielding device does not form a clean room boundary at least in a region in which the radiation shielding device extends along a path on which a holding device of the first transport device is movable.

16. The container treatment apparatus according to claim 1, wherein the second transport device is part of a container surface sterilization device, in particular a container outer surface sterilization device.

17. The container treatment apparatus according to claim 1, wherein the radiation shielding device has, in a first radiation shielding region which is arranged along the transport path upstream of a transfer point or transfer region at which containers can be transferred from a holding device of the first transport device to a holding device of the second transport device, a larger cross-section in at least one direction arranged perpendicularly to the transport path than in a second radiation shielding region in which the holding device of the first transport device is movable after the transfer of a container to a holding device of the second transport device.

18. The container treatment apparatus according to claim 1, wherein the radiation shielding device is formed in two parts and comprises an upper radiation shielding device part and a lower radiation shielding device part.

19. The container treatment apparatus according to claim 1, wherein an opening is provided in the upper radiation shielding device part, through which a fluid can be guided into the transfer region.

20. The container treatment apparatus according to claim 1, wherein the container treatment apparatus is in turn a sterilization device, having a container outer sterilization by the radiation source and a container inner sterilization in the region of the transport device.

* * * * *